United States Patent
Wang

(10) Patent No.: US 9,943,650 B2
(45) Date of Patent: Apr. 17, 2018

(54) RETRACTABLE SELF-DESTRUCTING SAFETY SYRINGE WITH PRE-ATTACHED NEEDLE

(71) Applicant: Zuyang Wang, Shanghai (CN)

(72) Inventor: Zuyang Wang, Shanghai (CN)

( * ) Notice: Subject to any disclaimer, the term of this patent is extended or adjusted under 35 U.S.C. 154(b) by 852 days.

(21) Appl. No.: 14/381,895

(22) PCT Filed: Feb. 26, 2013

(86) PCT No.: PCT/CN2013/000189
§ 371 (c)(1),
(2) Date: Dec. 31, 2014

(87) PCT Pub. No.: WO2013/127258
PCT Pub. Date: Sep. 6, 2013

(65) Prior Publication Data
US 2015/0157805 A1 Jun. 11, 2015

(30) Foreign Application Priority Data
Feb. 29, 2012 (CN) ..................... 2012 2 0071139 U

(51) Int. Cl.
*A61M 5/32* (2006.01)
(52) U.S. Cl.
CPC ........... *A61M 5/322* (2013.01); *A61M 5/3202* (2013.01); *A61M 2005/3224* (2013.01); *F04C 2270/0421* (2013.01)
(58) Field of Classification Search
CPC .......... A61M 5/322; A61M 2005/3224; A61M 5/3202
See application file for complete search history.

(56) References Cited

U.S. PATENT DOCUMENTS

| | | |
|---|---|---|
| 5,242,400 A | 9/1993 | Blake, III et al. |
| 5,968,020 A | 10/1999 | Saito |

(Continued)

FOREIGN PATENT DOCUMENTS

| | | |
|---|---|---|
| CN | 2750815 Y | 1/2006 |
| CN | 1803212 A | 7/2006 |

(Continued)

*Primary Examiner* — Nathan R Price
*Assistant Examiner* — Melissa A Snyder
(74) *Attorney, Agent, or Firm* — Muncy, Geissler, Olds & Lowe, P.C.

(57) ABSTRACT

A retractable self-destructing safety syringe with pre-attached needle including a barrel, an inner needle base disposed in a barrel neck at an end of the barrel body, and an elastic engagement mechanism formed between the barrel neck and the inner needle base is provided. An asymmetric elastic locking member having an elastic function is disposed at the end of the plunger, with which a sleeve-type retractable locking member on the needle base can be interlocked by the elastic function. After being retracted into the barrel body, the needle base together with the needle will be forced to deflect to one side under an asymmetric force, and the needle therefore will be forced to incline in a direction nearly a 45 degree angle toward to one side of the inner wall of the barrel and is blocked by the barrel neck, so that the needle and the needle base could not be pushed out the barrel neck again and self-destruction of the syringe is truly achieved. The asymmetric elastic locking member is a plastic hook which is formed with the plunger body by one-time molding process.

9 Claims, 6 Drawing Sheets

(56) References Cited

U.S. PATENT DOCUMENTS

| | | |
|---|---|---|
| 7,637,890 B2 | 12/2009 | Lin |
| 2002/0177820 A1 | 11/2002 | Wu |
| 2003/0040721 A1* | 2/2003 | Lee ..................... A61M 5/322 |
| | | 604/240 |
| 2004/0186427 A1 | 9/2004 | Pok |
| 2009/0171285 A1 | 7/2009 | Wang |
| 2013/0345630 A1 | 12/2013 | Jiang |

FOREIGN PATENT DOCUMENTS

| | | | |
|---|---|---|---|
| CN | 1986013 | A | 6/2007 |
| CN | 201076648 | Y | 6/2008 |
| CN | 101411908 | A | 4/2009 |
| CN | 101862490 | A | 10/2010 |
| CN | 202105269 | U | 1/2012 |
| CN | 202569090 | U | 12/2012 |
| JP | 2008528067 | A | 7/2008 |

* cited by examiner

RETRACTABLE SELF-DESTRUCTING SAFETY SYRINGE WITH PRE-ATTACHED NEEDLE

BACKGROUND OF THE INVENTION

Field of the Invention

The present invention relates to a technical field of medical devices, more particularly to a retractable self-destructing safety syringe with a pre-attached needle, and especially to the mechanical connection structure thereof.

Description of Related Art

Reference Document 1, with Patent No.: ZL200710047077.4, by Application Date: 2007 Oct. 16, with Issued No.: CN101411908, the patentee thereof: Shanghai Dingjiantang Biochemical Technology Co., Ltd., has disclosed a self-destructing safety vaccine syringe comprising a barrel body, a plunger disposed in the barrel body, a rubber piston disposed near an end of the plunger, a needle base disposed in a barrel neck of the barrel body, and a needle disposed on the needle base, which is characterized in that: a lateral notch is formed on a side wall of the end of a plunger body which is interconnected with a vertical notch formed at the end of the plunger body of the plunger and coupled with the vertical notch; an upper needle part and a lower part of the needle base are sleeved together to form the needle base, wherein the lower needle base is cylindrical and has a hollow cavity and a lower needle base rib is disposed on an inner wall of the lower needle base and located near an opening of the end of the lower needle base opposite the end at which the upper needle base is disposed; an elastic member formed by interconnecting the lateral notch with the vertical notch is disposed at the end of the plunger where the plunger body has a specific elasticity, wherein the vertical notch is narrow at the top and wide at the bottom while the outer wall of the plunder body above the outer opening of the lateral notch protrudes beyond an outer wall of the plunger body therebelow, the outer opening of the lateral notch is high and the inner opening thereof is low, and the end of the plunger is in a curved shape; the upper needle base is cylindrical, wherein a plurality of reinforcing fins is disposed on the outer wall of the upper portion of the upper needle base and a flange ring of the upper needle base is disposed on the outer wall of the lower portion of the upper needle base, and the outer diameter of the flange ring of the upper needle base is greater than the diameter of the outer wall of the upper needle base by 0.05 mm to 0.3 mm; the lower needle base is cylindrical and has a hollow cavity, wherein an annular locking groove of the lower needle base is disposed on the inner wall of the cavity of the lower needle base and is coupled with the flange ring of the upper needle base, the inner diameter of the cavity above the annular locking groove of the lower needle base is less than the outer diameter of the outer wall of the plunger body above the flange ring of the upper needle base by 0.1 mm to 0.35 mm while the inner diameter of the cavity below the annular locking groove of the lower needle base is less than or equals to the outer diameter of the outer wall of the plunger body below the flange ring of the upper needle base, and an annular rib of the lower needle base is disposed on the outer wall of an end of the lower needle base opposite the end of the lower needle base rib; an upper stopping ring of the barrel neck and a lower stopping ring of the barrel neck are respectively disposed on the inner wall of the barrel neck of the barrel body And the distance between the upper stopping ring of the barrel neck and the lower stopping ring of the barrel neck is ranged from 0.3 mm to 1.5 mm, wherein the upper stopping ring of the barrel neck protrudes beyond the inner wall between the upper stopping ring of the barrel neck and the lower stopping ring of the barrel neck by 0.1 mm to 0.6 mm, the lower stopping ring of the barrel neck protrudes beyond the inner wall between the upper stopping ring of the barrel neck and the lower stopping ring of the barrel neck by 0.02 mm to 0.25 mm, the inner diameter of the barrel cavity above the upper stopping ring of the barrel neck is greater than or equals to an inner diameter of the barrel cavity between the upper stopping ring of the barrel neck and the lower stopping ring of the barrel neck while the inner diameter of the barrel cavity between the upper stopping ring of the barrel neck and the lower stopping ring of the barrel neck is less than or equals to the inner diameter of the barrel cavity below the lower stopping ring of the barrel neck, the inner diameter of the barrel cavity between the upper stopping ring of the barrel neck and the lower stopping ring of the barrel neck is less than the outer diameter of the annular rib of the lower needle base by 0.1 mm to 0.5 mm; a stopping rib of the barrel body is disposed on the inner wall of the barrel cavity at an end opposite the end of the barrel neck and can be a linear annular rib, an annular rib consisting of several vertical ribs, a vertical rib, or an annular rib consisting of multiple protruding points; and an inner rib of the barrel body is disposed on the inner wall of the barrel body below the stopping rib of the barrel body, wherein the distance between the stopping rib of the barrel body and the inner rib of the barrel body is greater than or equals to the thickness of the annular pre-stopper piece and the inner diameter of the stopping rib of the barrel body is smaller than the diameter of the annular pre-stopper piece.

Reference Document 2, with Patent No.: ZL200720067715.4, by Application Date: 2007 Mar. 8, with Issued No.: CN201076648, the patentee thereof: Shanghai Dingjiantang Biochemical Technology Co., Ltd., has disclosed "a plunger with a metal hook" comprising a plunger body, a columnar locking member disposed on an upper end of the plunger body, and a rubber piston sleeved with the columnar locking member, which is characterized in that a mounting hole with a hook inside is disposed on the end of the plunger body at the position corresponding to the rubber piston.

Current safety syringes bear a function of retracting the needle by the hook to realize safe injections. The hook is generally made of metal pieces or plastic pieces. The metal piece requires manufacture process so as to match or be assembled on the plunger. The manufacturing process is complicated and difficult plus uncertainty of stability. Not only are the manufacturing process and cost increased, but the metal piece itself and the assembly process thereof will increase the uncertainty of risks in respect of product safety and quality. The current plastic hook still has structural defects or deficiencies, thereby leading to safety risks or vulnerabilities during use. Though the design of current plastic locking can fulfill the needle-retracting function, the needle still remains on the regular track after being retracted during use, so that it is possible to push out the needle again, which poses a risk of secondary injuries to the user.

In addition, a common problem existing in both current retractable self-destructing safety syringe with a single needle base and the current safety syringes is how to stabilize the locking stability between an inner needle base and a barrel body to the extent satisfying stability requirements, meanwhile the pulling force for retracting the needle base should not be excessive for purpose of user's comfort and convenient use. Although the rigid locking structures can achieve a stable locking effect between the inner needle base and the inner wall of the barrel body, it is hard or even impossible to meet the requirement for convenient use at the same time. The instability of plastic materials and the tendency to be easily affected by environmental temperature lead to poor stability of the products with rigid locking structures, which makes it quite difficult to control the quality and precision during the production process and makes it impossible to realize mass production.

As mentioned above, it is still necessary to further improve the structure of the plunger and the locking structure between the inner needle base and the barrel body of the current retractable syringe, thereby further improving safety and stability during use, and achieving the purposes of simplifying the manufacturing process and reducing the manufacturing cost.

BRIEF SUMMARY OF THE INVENTION

The object of the present invention is to provide a retractable self-destructing safety syringe with pre-attached needle. An inner needle base inside the syringe and a barrel body of the syringe are interlocked with each other by an elastic buffering mechanism. The locking and releasing effects therebetween are perfectly achieved by skillfully utilizing the buffering gap at the locking position and the plasticity of the locking parts. The elastic buffering mechanism can be formed either on the inner needle base or on the inner wall of the barrel body, meanwhile, an corresponding engagement structure is formed either on the inner wall of the barrel body or on the inner needle base. An end of the plunger body is provided with an asymmetric locking member which has elastic functionality and can be interlocked with the cavity of the needle base of the syringe through engagement. After being retracted back into the barrel body of the syringe, the needle base is forced to deflect toward to one side under a force generated from the asymmetrical elastic mechanism, the needle therefore inclines in a direction nearly a 45 degree angle to one side of the inner wall of the barrel body and then is blocked by the barrel neck of the barrel body, so that the needle and the needle base could not be pushed out of the barrel neck again. Therefore, the needle is effectively prevented from being pushed out of the barrel again which may cause secondary injuries, so that to achieve operating safety and self-destruction of the syringe, thereby to overcome and improve defects and deficiencies in the prior arts.

In order to achieve above objects, the main technical solution of the present invention is to provide a retractable self-destructing safety syringe with pre-attached needle. The retractable self-destructing safety syringe with pre-attached needle comprises a barrel body, a needle base body disposed in the barrel neck at the end of the barrel body, a plunger disposed in the barrel body, a rubber piston disposed near the end of the plunger. It is characterized in that: The upper part of the needle base body is located in the barrel neck, the middle part of the needle base body forms an elastic sealing engaging portion, and the lower part of the needle base body is connected with a sleeve-type retractable locking member elastic sealing engaging portion. An annular buffering gap is located on a surface of the elastic sealing engaging portion, a ring-shaped engagement part is formed on the outer wall of the elastic sealing engaging portion outside the annular buffering gap. An asymmetric elastic locking member is disposed at the end of the plunger body.

The present invention discloses a retractable self-destructing safety syringe with pre-attached needle. The asymmetric locking member with elastic function is disposed at the end of the plunger body. A combination design of the asymmetrical structure with elastic functionality can ensure that the asymmetric elastic locking member can be smoothly inserted into the cavity of the needle base, and the interlocking between the asymmetrical locking member and a locking part of the sleeve-type retractable locking member in the needle base cavity is realized through a elastic expansion mechanism. Since the annular recess in the cavity of the sleeve-type retractable locking member also has elastic and buffering characteristic, when it contacts the asymmetric elastic locking member with being pushed, buffering and deformation correspondingly happens to both, so that the asymmetric elastic locking member can stuck into the cavity of the sleeve-type retractable locking member and be interlocked with the sleeve-type retractable locking member when the asymmetric elastic locking member is being retracted. After being retracted back into the barrel body of the syringe, the needle base will be deflected to a side under a asymmetrical force, the needle therefore inclines in a direction nearly a 45 degree angle to one side of the inner wall of the barrel body and be blocked by the barrel neck of the barrel body, so that the needle and the needle base cannot be pushed out of the barrel neck again. Therefore, the needle is prevented from being pushed out of the barrel neck again which may cause secondary injuries to achieve operating safety and self-destruction of the syringe. In the embodiment of the present invention, the asymmetric elastic locking member is a plastic hook. The design of the plastic hook adopts a combination of asymmetrical and elastic structure together with applications of specific angles and sizes, and enables the plastic hook to perform both functions of buffering and interlocking. The above mentioned asymmetric elastic locking member is integrated together with the plunger body and is formed by one-time molding process, which has no need for separated manufacturing and follow-up assembly. This design can significantly reduce manufacture costs and simplify assembly processes and procedures. The product is easy to use and functionally stable. Interlocking function between the asymmetric elastic locking member at the end of the plunger and the cavity of the inner needle base is very effective and stable. Overall and integral structure design of the product is ingenious with reasonable rationale, which makes the product easy to use and has wide application potentials. In comparison with designs and techniques of current products, the present invention has significant technical breakthroughs and brought the product unique safety features and practicability.

DETAILED DESCRIPTION OF THE PREFERRED EMBODIMENT

Figure 1:
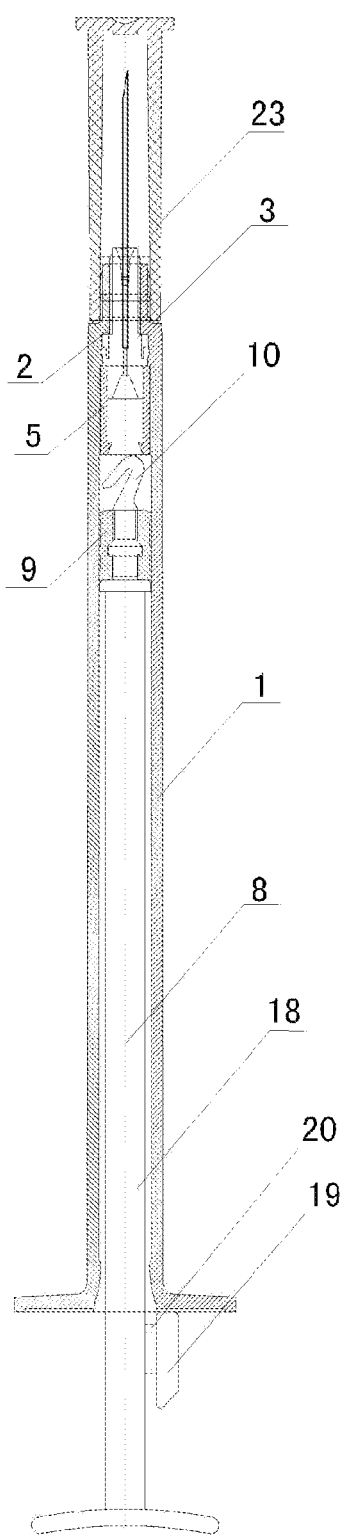
FIG. 1 is a schematic diagram of the present invention.
Figure 2:
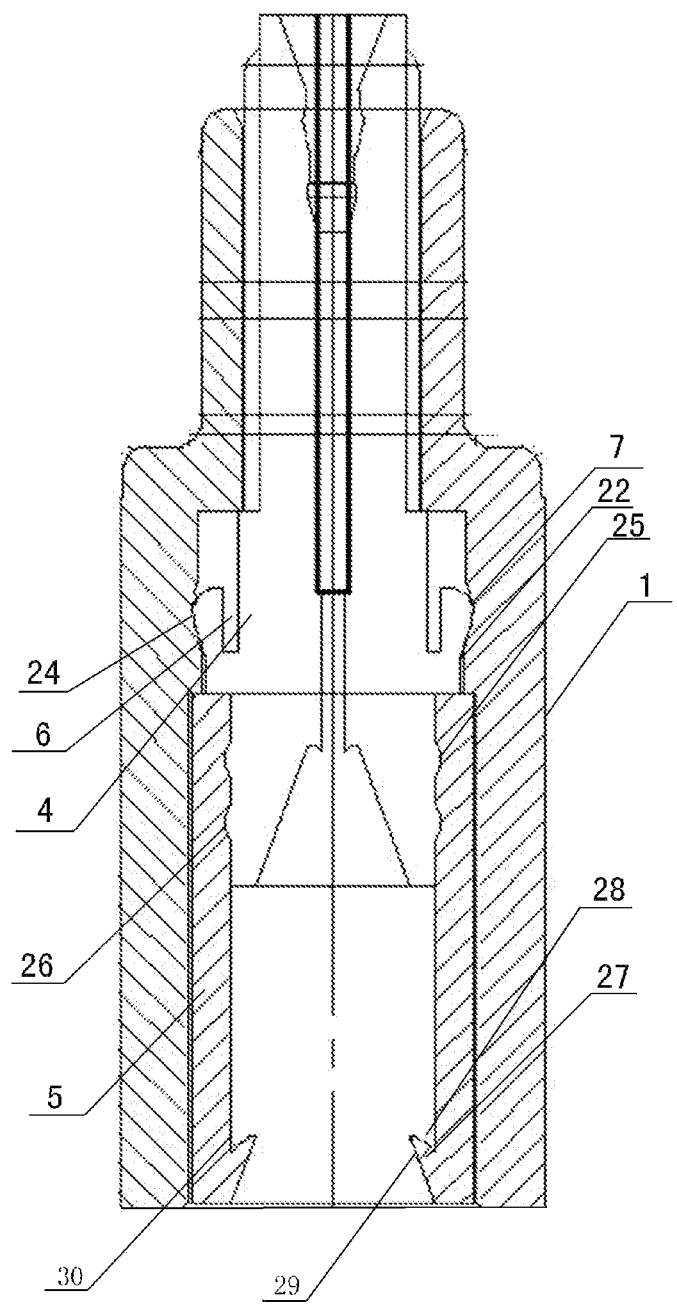
FIG. 2 is an assembly diagram of a needle base body and a sleeve-type retractable locking member of the present invention.

Hereinafter, preferred embodiments of the present disclosure will be described in detail with reference to the accompanying drawings.

The present invention is a retractable self-destructing safety syringe with pre-attached needle, which comprises a barrel body 1, a needle base body 3 disposed in the barrel neck 2 at the end of the barrel body 1, a plunger 8 disposed in the barrel body 1, and a rubber piston 9 disposed near the end of plunger 8. It differs from current techniques in that: the upper part of the needle base body 3 is located in the barrel neck 2, the middle part of the needle base body 3 forms an elastic sealing engaging portion 4, and the lower part of the needle base body 3 is connected with a sleeve-type retractable locking member 5, wherein an annular buffering gap 6 is located on the surface of the elastic sealing engaging portion 4, a ring-shaped engagement part 7 is formed on the outer wall of the elastic sealing engaging portion 4 outside the annular buffering gap 6 and an asymmetric elastic locking member 10 is disposed at the end of the plunger 8. The needle base and the barrel body can be interlocked effectively and released easily due to the elastic engagement structure.

An elastic mechanism can be formed on one side or both sides of the above mentioned asymmetric elastic locking member, in addition, the outer side part of the elastic mechanism at one side of the asymmetric elastic locking member should protrudes beyond the side wall of the junction between the asymmetric elastic locking member and the plunger body, thereby to achieve and ensure locking effect and deflection function among the asymmetric elastic locking member and the needle base.

In a detailed embodiment, the asymmetric elastic locking member 10 is a hook. The hook is made of plastic material, which is integrated together with the plunger body 8 and is formed by one-time molding process. Or, the hook and the plunger body 8 are independent parts to form a split-type assembly structure.

In a detailed embodiment, the hook can also be assembled at the end of the plunger though other assembly structures.

In a detailed embodiment, a base portion 11 is formed at the lower end of the hook, a first arm 12 deflecting to one side is formed at the upper part of the base portion 11, a concave curve shaped angle 13 or a corner is defined by the outer sidewall of the junction between the first arm 12 and the base portion 11, and the concave curve shaped angle 13 is ranged from 45 to 179 degrees. The lower end of the first arm 12 is connected with the upper end of the base portion 11, the upper end of the first arm 12 is connected with one end of a second arm 14 and another end of the second arm 14 is in a suspended condition. A curve shaped surface 15 is formed on the outer side of the junction between the first arm 12 and the arm 14, the inner angle 17 ranged from 2 to 90 degrees is defined by an inner side of the junction between the first arm 12 and the second arm 14. The width of the opening formed between the suspended end of the second arm 14 and the first arm 12 is ranged from 0.5 mm to 40 mm. The length of the first arm 12 is ranged from 0.5 mm to 50 mm, the length of the second arm 14 is ranged from 0.5 mm to 60 mm. Only the structure designed in such a way can achieve and ensure locking effect and deflection function among the hook and the needle base.

In a specific embodiment, four reinforcing ribs 18 arranged in a cross shape and at equal angles are formed on the plunger body 8, with a pre-stopper piece 19 disposed on the outer edge of the reinforcing ribs 18. The pre-stopper piece 19 is connected with the reinforcing ribs 18 by at least two connection portions 20. After the syringe is assembled, the top end of the pre-stopper piece is just against on the lower end of the barrel body thereby preventing the syringe from accidental uselessness caused by forward movement of the plunger. The pre-stopper piece can be removed from the reinforcing ribs simply by bending the pre-stopper piece along the connection portions when starting to use the syringe.

In a detailed embodiment, the annular buffering gap 6 is an annular groove-like structure, the height from the opening of the groove to the bottom of the groove is ranged from 0.05 mm to 4 mm, the width of the annular buffering gap 6 is ranged from 0.05 mm to 4 mm. The distance from the outer groove wall of the annular buffering gap 6 to the top of the curve shaped surface of the ring-shaped engagement part 7 is ranged from 0.1 mm to 6 mm. The distance from the opening of the outer groove wall of the annular buffering gap 6 to the outer wall of the ring-shaped engagement part 7 is ranged from 0.1 mm to 6 mm, and the distance from the bottom of the outer groove wall of the annular buffering gap 6 to the outer wall of the ring-shaped engagement part 7 is ranged from 0.1 mm to 6 mm. The surface of the ring-shaped engagement part 7 is a curve shaped surface, and the distance from the top of the curve shaped surface of the ring-shaped engagement part 7 to the upper edge of the curve shaped surface is less than the distance from the top of the curve shaped surface of the ring-shaped engagement part 7 to the lower edge of the curve shaped surface. An annular recess 22 is formed on the outer wall of the elastic sealing engaging portion 4 below the ring-shaped engagement part 7.

In a detailed embodiment, the annular recess 22 is on the same horizontal plane as the groove bottom of the annular buffering gap 6 is, or higher than the groove bottom of the annular buffering gap 6.

In a detailed embodiment, the exterior of the barrel neck 2 of the barrel body 1 is covered by a barrel body cap 23.

In a detailed embodiment, an annular engagement sealing recess 24 corresponding to the ring-shaped engagement part 7 is disposed on the inner wall of the barrel neck 2 of the barrel body 1. The depth of the annular engagement sealing recess 24 is ranged from 0.01 mm to 4 mm, the height of the annular engagement sealing recess 24 is ranged from 0.01 mm to 6 mm, and the recess bottom of the annular engagement sealing recess 24 is a curve shaped surface.

In a detailed embodiment, at least one flange ring 25 is formed on the outer wall of the needle base body 3, and an annular engagement groove 26 corresponding to the flange ring 25 is disposed on the inner wall of the sleeve-type retractable locking member 5.

In a detailed embodiment, the sleeve-type retractable locking member 5 has an inner hollow cavity, a ring-shaped engaging and locking portion 27 is formed on the inner wall of the cavity near the opening of the lower end of the sleeve-type retractable locking member 5.

In a detailed embodiment, an annular groove 28 is formed on the upper side of the ring-shaped engaging and locking portion 27. The thickness of the inner side wall 29 under the annular groove 28 is ranged from 0.01 mm to 3 mm, an angle ranged from 2 to 90 degrees is formed between the inner side wall of the annular groove 28 and the outer sidewall 30 of the annular groove 28, the inner diameter at the upper end of the inner side wall of the annular groove 28 is ranged from 1 mm to 80 mm, and the width at the open side of the annular groove 28 is greater than the width at the bottom side of the annular recess.

Figure 3:
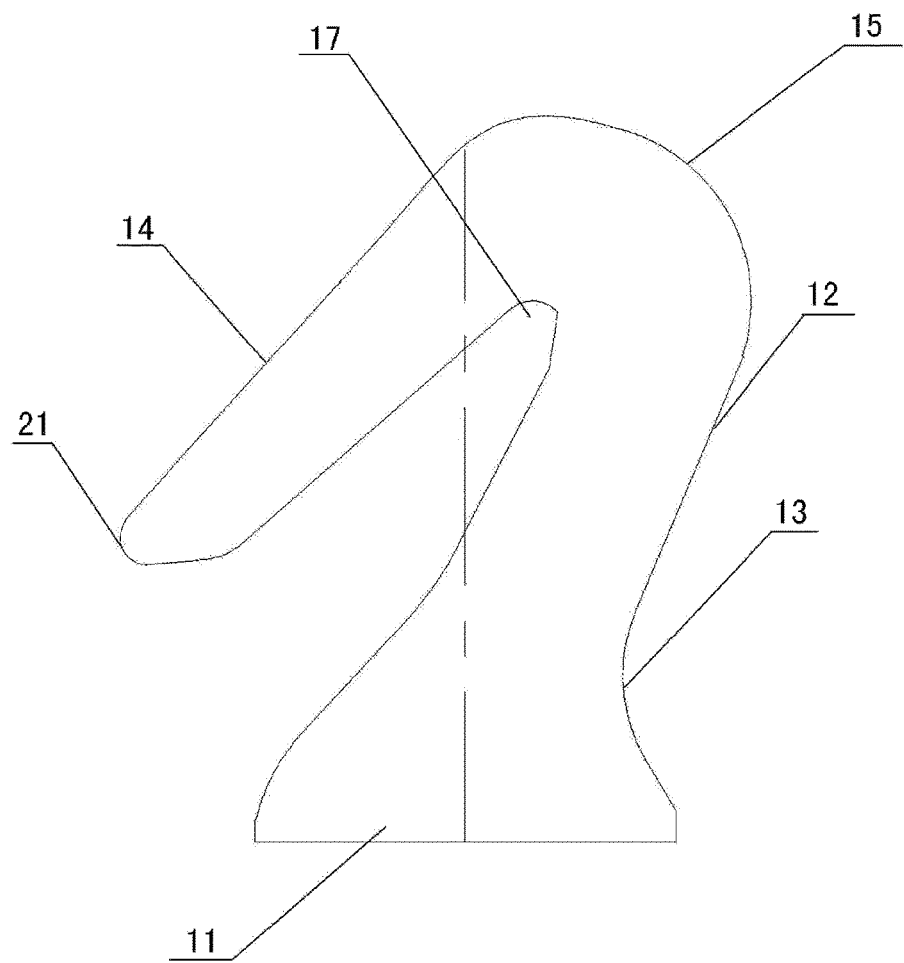
FIG. 3 is a schematic diagram of the hook of the present invention.
Figure 4:
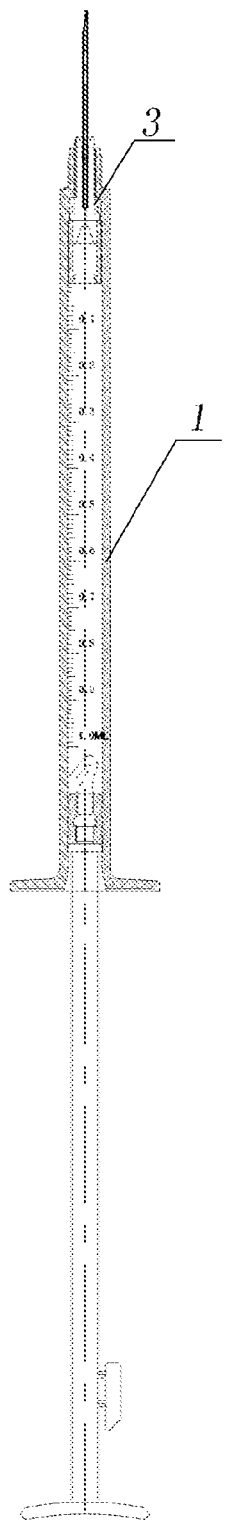
FIG. 4 is a diagram of a first use state of the present invention.
Figure 5:
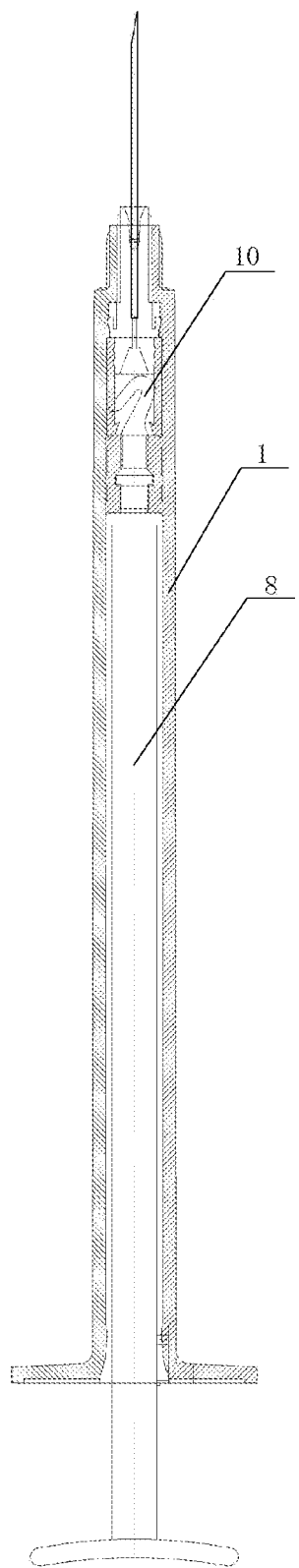
FIG. 5 is a diagram of a second use state of the present invention.
Figure 6:
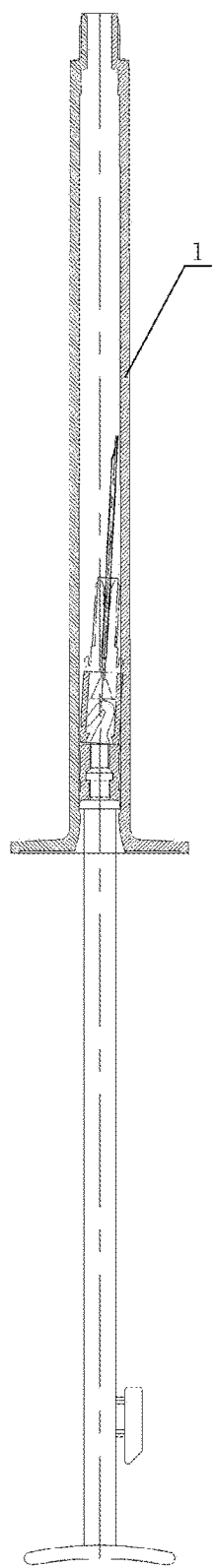
FIG. 6 is a diagram of a third use state of the present invention.

In practical operation, as shown in FIG. 3 to FIG. 4, draw liquid and begin injection, as pushing the plunger forward slowly until the asymmetric elastic locking member contacts with the sleeve-type retractable locking member, because the total width of the asymmetrical elastic retracting locking member is greater than the inner diameter of the annular groove in the sleeve-type retractable locking member, one side of the asymmetric elastic locking member is deformed to narrow its width and then the asymmetrical elastic retracting locking member enters the cavity of the internal sleeved retracting locking member. After the asymmetric elastic locking member enters into the cavity and pushing force is released, the asymmetric elastic locking member restores to its original state (and interlocked with the needle base). Pull the plunger backwards when injection is finished, the side end of the asymmetric elastic locking member (the suspended end of the second arm of the hook) shall stick into the annular groove of the sleeve-type retractable locking member. Under the pulling force from the plunger, which is transferred to the needle base body through the internal sleeved retracting locking member, the annular buffering gap on the side of the elastic sealing engaging portion on the needle base body is deformed and narrowed down, and then the ring-shaped engagement part slides out from the annular engagement sealing recess of the barrel body. At the end, the needle base together with the needle is pulled back into the barrel. The needle is deflected toward to one side under a force generated from the asymmetric elastic locking member and is deviated from a regular moving track, therefore the needle together with the needle base cannot be restored back into the barrel neck again, so as to achieve operating safety and self-destruction of the syringe.

The above contents describe the present invention in a combination of detailed and preferred embodiment methods. However, it should not be considered that the detailed and preferred embodiment of the present invention is limited only to the above descriptions. A person of ordinary skill in the art, without departing from the concept of the present invention, may make several simple derivations or alternatives which should be deemed and included within the scope of the present invention.

What is claimed is:

1. A retractable self-destructing safety syringe with pre-attached needle, comprising a barrel body (1), a needle base body (3) disposed in a barrel neck(2) at the end of the barrel body (1), a plunger (8) disposed in the barrel body (1), and a rubber piston (9) disposed near the end of the plunger (8), wherein the upper part of the needle base body (3) is located in the barrel neck (2), the middle part of the needle base body (3) forms an elastic sealing engaging portion (4), and the lower part of the needle base body (3) is connected with a sleeve-type retractable locking member (5), wherein an annular buffering gap (6) is located on the surface of the elastic sealing engaging portion (4), a ring-shaped engagement part (7) is formed on the outer wall of the elastic sealing engaging portion (4) outside the annular buffering gap (6), and an asymmetric elastic locking member (10) is disposed on the end of the plunger (8), wherein the asymmetric elastic locking member (10) is a hook, the hook is made of plastic material, and the hook is integrated together with the plunger body (8) and is formed by one-time molding process; or the hook and the plunger body (8) are independent parts to form a split-type assembly structure, and wherein a base portion (11) is formed at the lower end of the hook, a first arm (12) deflecting to one side is formed at the upper part of the base portion (11); a concave curve shaped angle (13) or corner is defined by the outer sidewall of the junction between the first arm (12) and the base portion (11) and the concave curve shaped angle (13) is ranged from 45 to 179 degrees, the lower end of the first arm (12) is connected with the upper end of the base portion (11), the upper end of the first arm (12) is connected with one end of a second arm (14) and another end of the second arm (14) is in a suspended condition, a curve shaped surface (15) is formed on the outer side of the junction between the first arm (12) and the second arm (14), the inner angle (17) ranged from 2 to 90 degrees is defined by an inner side of the junction between the first arm (12) and the second arm (14), the width of the opening formed between the suspended end of the second arm (14) and the first arm (12) is ranged from 0.5 mm to 40 mm, the length of the first arm (12) is ranged from 0.5 mm to 50 mm, the length of the second arm (14) is ranged from 0.5 mm to 60 mm; a tip (21) is formed at the suspended end of the second arm (14), and the suspended end of the second arm (14) protrudes beyond the outer edge of the base portion (11).

2. The retractable self-destructing safety syringe with pre-attached needle as claimed in claim 1, wherein four reinforcing ribs (18) arranged in a cross shape and at equal angles are formed on the plunger body (8), a pre-stopper piece (19) is disposed on the outer edge of the reinforcing ribs (18), and the pre-stopper piece (19) is connected with the reinforcing ribs (18) by at least two connecting portions (20).

3. The retractable self-destructing safety syringe with pre-attached needle as claimed in claim 1, wherein the annular buffering gap (6) is an annular groove-like structure, the height from the opening of the groove to the bottom of the groove is ranged from 0.05 mm to 4 mm, the width of the annular buffering gap (6) is ranged from 0.05 mm to 4 mm, the distance from the outer groove wall of the annular buffering gap (6) to the top of the curve shaped surface of the ring-shaped engagement part (7) is ranged from 0.1 mm to 6 mm, the distance from the opening of the outer groove wall of the annular buffering gap (6) to the outer wall of the ring-shaped engagement part (7) is ranged from 0.1 mm to 6 mm, the distance from the bottom of the outer groove wall of the annular buffering gap (6) to the outer wall of the ring-shaped engagement part (7) is ranged from 0.1 mm to 6 mm, the surface of the ring-shaped engagement part (7) is a curve shaped surface, the distance from the top of the curve shaped surface of the ring-shaped engagement part (7) to the upper edge of the curve shaped surface is less than the distance from the top of the curve shaped surface of the ring-shaped engagement part (7) to the lower edge of the curve shaped surface, and an annular recess (22) is formed on the outer wall of the elastic sealing engaging portion (4) below the ring-shaped engagement part (7).

4. The retractable self-destructing safety syringe with pre-attached needle as claimed in claim 1, wherein the annular recess (22) is on the same horizontal plane as the groove bottom of the annular buffering gap (6) is, or higher than the groove bottom of the annular buffering gap (6).

5. The retractable self-destructing safety syringe with pre-attached needle as claimed in claim 1, wherein the exterior of the barrel neck (2) of the barrel body (1) is covered by a barrel body cap (23), an annular engagement sealing recess (24) corresponding to the ring-shaped engagement part (7) is disposed on the inner wall of the barrel neck (2) of the barrel body (1), the depth of the annular engagement sealing recess (24) is ranged from 0.01 mm to 4 mm, the height of the annular engagement sealing recess (24) is ranged from 0.01 mm to 6 mm, and the recess bottom of the annular engagement sealing recess (24) is a curve shaped surface.

6. The retractable self-destructing safety syringe with pre-attached needle as claimed in claim 1, wherein at least one flange ring (25) is formed on the outer wall of the needle base body (3), and an annular engagement groove (26) corresponding to the flange ring (25) is disposed on the inner wall of the sleeve-type retractable locking member (5).

7. The retractable self-destructing safety syringe with pre-attached needle as claimed in claim 1, wherein the sleeve-type retractable locking member (5) has a inner hollow cavity, and a ring-shaped engaging and locking portion (27) is formed on the inner wall of the cavity near the opening of the lower end of the sleeve-type retractable locking member (5).

8. The retractable self-destructing safety syringe with pre-attached needle as claimed in claim 1, wherein an annular groove (28) is formed on the upper side of the ring-shaped engaging and locking portion (27), the thickness of the inner side wall (29) under the annular recess (28) is ranged from 0.01 mm to 3 mm, an angle ranged from 2 to 90 degrees is formed between the inner side wall of the annular recess (28) and the outer side wall (30) of the annular groove (28), and the inner diameter at the upper end of the inner side wall of the annular groove (28) is ranged from 1 mm to 80 mm.

9. The retractable self-destructing safety syringe with pre-attached needle as claimed in claim 1, wherein the width at the opening of the annular groove (28) is greater than the width at the bottom of the annular groove (28).

* * * * *